United States Patent
Liu et al.

(10) Patent No.: US 11,292,761 B2
(45) Date of Patent: Apr. 5, 2022

(54) METHOD FOR DIRECTLY PRODUCING METHYL ACETATE AND/OR ACETIC ACID FROM SYNGAS

(71) Applicant: DALIAN INSTITUTE OF CHEMICAL PHYSICS, CHINESE ACADEMY OF SCIENCES, Dalian (CN)

(72) Inventors: Hongchao Liu, Dalian (CN); Wenliang Zhu, Dalian (CN); Zhongmin Liu, Dalian (CN); Yong Liu, Dalian (CN); Shiping Liu, Dalian (CN); Fuli Wen, Dalian (CN); Youming Ni, Dalian (CN); Xiangang Ma, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

(21) Appl. No.: 16/647,174

(22) PCT Filed: Sep. 29, 2017

(86) PCT No.: PCT/CN2017/104609
§ 371 (c)(1),
(2) Date: Mar. 13, 2020

(87) PCT Pub. No.: WO2019/061358
PCT Pub. Date: Apr. 4, 2019

(65) Prior Publication Data
US 2020/0239401 A1 Jul. 30, 2020

(51) Int. Cl.
*B01J 8/04* (2006.01)
*B01J 8/06* (2006.01)
(Continued)

(52) U.S. Cl.
CPC .............. *C07C 67/36* (2013.01); *B01J 8/0492* (2013.01); *B01J 8/065* (2013.01); *B01J 23/002* (2013.01);
(Continued)

(58) Field of Classification Search
None
See application file for complete search history.

(56) References Cited

U.S. PATENT DOCUMENTS 6,127,432 A * 10/2000 Wegman ................. C07C 51/12
518/715
2007/0238897 A1* 10/2007 Cheung ................... C07C 51/09
560/232

(Continued)

FOREIGN PATENT DOCUMENTS

| CN | 1295550 A | 5/2001 |
| CN | 101910099 A | 12/2010 |

(Continued)

OTHER PUBLICATIONS

Ott ("Methanol" Ullmann's Encyclopedia of Industrial Chemistry, https://doi.org/10.1002/14356007.a16_465.pub3, 2012, p. 1-27) (Year: 2012).*

(Continued)

*Primary Examiner* — Amy C Bonaparte
(74) *Attorney, Agent, or Firm* — Maier & Maier, PLLC

(57) ABSTRACT

A method for directly producing methyl acetate and/or acetic acid from syngas, carried out in at least two reaction zones, including: feeding a raw material containing syngas into a first reaction zone to contact and react with a metal catalyst; allowing an obtained effluent to enter a second reaction zone directly or after the addition of carbon monoxide so as to contact and react with a solid acid catalyst; separating the obtained effluent to obtain product of acetate and/or acetic (Continued)

acid, and optionally returning a residual part to enter the first reaction zone and/or the second reaction zone to recycle the reaction. By the method above, the product selectivity of the product of methyl acetate or acetic acid is greater than 93%, and the quantity of methyl acetate and acetic acid may be adjusted according to processing.

6 Claims, 2 Drawing Sheets

(51) Int. Cl.
  *B01J 29/70*    (2006.01)
  *C07C 51/10*    (2006.01)
  *C07C 67/36*    (2006.01)
  *B01J 23/00*    (2006.01)
  *B01J 23/889*    (2006.01)
  *B01J 29/18*    (2006.01)
  *B01J 29/40*    (2006.01)

(52) U.S. Cl.
  CPC ............ *B01J 23/8892* (2013.01); *B01J 29/18* (2013.01); *B01J 29/40* (2013.01); *B01J 29/70* (2013.01); *B01J 29/7023* (2013.01); *C07C 51/10* (2013.01); *B01J 2208/025* (2013.01)

(56) References Cited

U.S. PATENT DOCUMENTS

| | | | | |
|---|---|---|---|---|
| 2008/0146833 A1* | 6/2008 | Iglesia | ................... | C07C 67/36 560/232 |
| 2009/0275774 A1* | 11/2009 | Law | ....................... | C07C 51/12 560/232 |
| 2013/0178671 A1 | 7/2013 | Lynch et al. | | |
| 2015/0298108 A1* | 10/2015 | Ni | ....................... | B01J 31/0244 560/232 |
| 2018/0201567 A1* | 7/2018 | Ni | ........................... | C07C 67/37 |
| 2018/0201568 A1* | 7/2018 | Liu | ....................... | C07C 29/172 |
| 2018/0370896 A1* | 12/2018 | Liu | ....................... | B01J 29/7069 |

FOREIGN PATENT DOCUMENTS

| | | | | |
|---|---|---|---|---|
| CN | 106365995 A | | 2/2017 | |
| CN | 106890665 | * | 6/2017 | |
| CN | 106890668 | * | 6/2017 | |
| CN | 106890669 | * | 6/2017 | |
| CN | 106890670 | * | 6/2017 | |
| CN | 106890671 | * | 6/2017 | |
| WO | WO-2017012244 A1 | * | 1/2017 | ............. C07C 69/24 |
| WO | WO-2017012245 A1 | * | 1/2017 | ............. B01J 35/04 |
| WO | WO-2017012246 A1 | * | 1/2017 | ............. C07C 67/37 |

OTHER PUBLICATIONS https://chem.libretexts.org/Bookshelves/Introductory_Chemistry/Book%3A_Introductory_Chemistry_Online_(Young)/09%3A_The_Gaseous_State/94%3A_The_Mole-Volume_Relationship%3A_Avogadros_Law (Year: 2020).*

Park ("Selective carbonylation of dimethyl ether to methyl acetate or Ferrierite" Catalysis Communications, 75, 2016, p. 28-31) (Year: 2016).*

Zhan ("Dimethyl ether carbonylation over zeolites" Journal of Energy Chemistry 36, 2019, p. 51-63) (Year: 2019).*

Ott ("Methanol" Ullmann's Encyclopedia of Industrial Chemistry, p. 1-27, 2012) (Year: 2012).*

International Search Report dated Jun. 27, 2018 in corresponding International application No. PCT/CN2017/104609; 6 pages.

* cited by examiner

METHOD FOR DIRECTLY PRODUCING METHYL ACETATE AND/OR ACETIC ACID FROM SYNGAS

FIELD

The present invention relates to a method for directly converting syngas to produce methyl acetate and/or acetic acid.

BACKGROUND

Methyl acetate is a colorless, scented liquid with less toxicity and strong dissolving ability, which is an excellent cellosolve and spray solvent. As an important intermediate in the chemical industry, methyl acetate can produce downstream products including ethanol, acetic acid, acetic anhydride, methyl acrylate, vinyl acetate, and acetamide, etc., and have a very broad application prospect.

Acetic acid is an important organic acid, which can be used in the production of vinyl acetate, acetic anhydride, cellulose acetate, acetates and metal acetates. Acetic acid is also used as a solvent and raw material in pesticides, pharmaceuticals and dyes and other industries. Acetic acid is widely used in pharmaceutical manufacturing, textile printing and rubber industries.

At present, the main synthesis methods of methyl acetate are: reactive distillation of methanol and acetic acid as raw materials; methanol dehydrogenation synthesis of methanol as raw material; one-step methanol carbonylation method of methanol and CO as raw materials; homologation of methyl formate and dimethyl ether carbonylation. The industrial production method of acetic acid is mainly carbonylation of methanol on Rh—I or Ir—I catalyst to generate acetic acid. Because this process uses precious metal catalysts, and there is also the production of hydrogen halide, the requirements for production equipment are extremely high.

The production of a large variety of basic chemical raw materials and high value-added fine chemicals using syngas as raw materials has been a hot topic in the field of catalysis. The direct preparation of ethanol from syngas is a new process for ethanol preparation in recent years. From the point of view of process and cost, the process of direct preparation of ethanol from syngas is short, the operating cost is relatively economical, and the investment cost is low. However, from the perspective of thermodynamics and kinetics, it is difficult for the reaction to stay on the target product, i.e. ethanol. Because the direct preparation of ethanol from syngas is a strong exothermic reaction, the first problem is to solve the problems of selectivity and tolerance. From the actual reaction results, the products are widely distributed. Not only there are a large number of C2 oxygenated by-products such as acetaldehyde and acetic acid, but also C2-C5 alkanes and olefins. The selectivity of ethanol is not ideal and the yield is low.

Although the rhodium-based catalyst has the performance of selectively synthesizing C2 oxygenated compounds by syngas. However, the use of precious metal such as rhodium has greatly increased the production cost of ethanol, and the production of rhodium is limited. There is great difficulty in large-scale promotion and application, which has become the bottleneck of the industrialization of this process route. Significantly reducing the use of rhodium or replacing rhodium with non-precious metal catalysts is an effective way to promote the industrialization of this technology, but progress is currently relatively slow.

Dalian Institute of Chemical Physics discloses a method for producing methyl acetate by carbonylation of dimethyl ether and carbon monoxide-containing feed gas in a reactor carrying an acidic EMT zeolite molecular sieve as a catalyst (CN106365995A). According to the relevant technology of Dalian Institute of Chemical Physics, a 100,000 ton coal-based ethanol project industrial demonstration project has been successfully put into operation and runs stably. However, the direct production of oxygenated compounds using syngas as the raw material has always been the focus of researchers. The invention uses syngas as the raw material to provide a new method for direct synthesis of methyl acetate and/or acetic acid from syngas, with high product selectivity, mild reaction conditions, simple process, and has great industrial application prospects.

SUMMARY

The purpose of the present invention is to overcome some or all of the problems in the prior art, and provide a novel technology for syngas conversion and a novel method for the production of methyl acetate and acetic acid.

To this end, the present invention provides a method for directly producing methyl acetate and/or acetic acid from syngas, whose reaction process is carried out in at least two reaction zones and the method comprises:

a) feeding a raw material containing syngas into a first reaction zone to contact with a metal catalyst in the first reaction zone, reacting to obtain an effluent containing methanol and/or dimethyl ether;

b) allowing the effluent from the first reaction zone to enter a second reaction zone directly or after the addition of carbon monoxide so as to contact with a solid acid catalyst in the second reaction zone and react to obtain an effluent containing methyl acetate and/or acetic acid;

c) separating the effluent from the second reaction zone to obtain product of acetate and/or acetic acid, and optionally returning a residual part to enter the first reaction zone and/or the second reaction zone to recycle the reaction;

wherein the volume content of syngas feed gas in the raw material is in a range from 10% to 100%, and the volume ratio of carbon monoxide to hydrogen in the syngas is in a range from 0.1 to 10;

the reaction temperature in the first reaction zone is in a range from 180° C. to 300° C., the reaction pressure is in a range from 0.5 MPa to 20.0 MPa; and the reaction temperature in the second reaction zone is in a range from 180° C. to 300° C., the reaction pressure is in a range from 0.5 MPa to 20.0 MPa.

Preferably, the metal catalyst in the first reaction zone is a catalyst for synthesis of methanol or dimethyl ether.

Preferably, the solid acid catalyst in the second reaction zone comprises one or more molecular sieves selected from FER, MFI, MOR, ETL, MFS, MTF, EMT zeolite molecular sieves and molecular sieve products obtained by modifying the zeolite molecular sieves using pyridine or elements other than the framework constituent elements.

Preferably, the solid acid catalyst is a hydrogen-type product of the zeolite molecular sieve, or is composed of ranging from 10% to 95% by weight of the hydrogen-type product and a remaining matrix, or is a molecular sieve product obtained by modifying the hydrogen-type product with pyridine; wherein the matrix is one or more selected from alumina, silica, kaolin and magnesia.

Preferably, the first reaction zone and/or the second reaction zone are in a fixed bed reactor, and the fixed bed reactor is preferably a tubular fixed bed reactor.

Preferably, the first reaction zone and the second reaction zone are in the same fixed reactor, or the first reaction zone and the second reaction zone are respectively in different reactors connected in series.

Preferably, the syngas in the raw material is composed of ranging from 50% to 100% by volume of carbon monoxide and hydrogen and ranging from 0% to 50% by volume of one or more inactive gases selected from nitrogen, helium, argon and carbon dioxide.

Preferably, the reaction temperature in the first reaction zone is in a range from 190° C. to 290° C. and the reaction pressure is in a range from 1.0 MPa to 15.0 MPa; and the reaction temperature in the second reaction zone is in a range from 190° C. to 290° C. and the reaction pressure is in a range from 1.0 MPa to 15.0 MPa.

The present invention includes but is not limited to the following beneficial effects:

1. This is provided a novel method for direct and directional synthesis of methyl acetate and/or acetic acid from syngas.

2. The method of the present invention has high product selectivity, mild reaction conditions, simple process, and has great industrial application prospects.

DETAILED DESCRIPTION OF THE EMBODIMENTS

Figure 1:
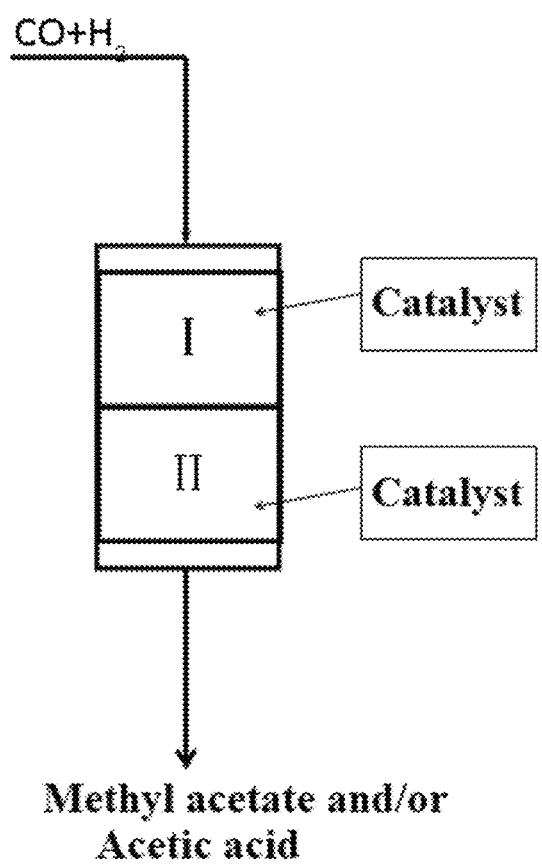
FIG. 1 is a flow chart of the direct preparation of methyl acetate/acetic acid from syngas according to an embodiment of the present invention, wherein the first reaction zone and the second reaction zone are in the same reactor.

Through the coupling of the catalyst and the novel reaction process, the present invention enables the syngas to use non-precious metal catalysts and molecular sieve catalysts to selectively produce methyl acetate and/or acetic acid under certain conditions, greatly simplifying the process of carbonylation to produce methyl acetate and/or acetic acid, reducing the production and operation costs, while opening up a novel method of direct syngas conversion.

The present invention provides a method for directly producing methyl acetate and/or acetic acid from syngas. The syngas raw material was passed through a reactor equipped with a metal catalyst such as a copper-based catalyst and a solid acid catalyst such as an acidic molecular sieve catalyst. Methyl acetate and/or acetic acid were produced under the conditions of a reaction temperature of ranging from 190° C. to 290° C., a reaction pressure of ranging from 0.5 MPa to 20.0 MPa and a space velocity of ranging from 1500 $h^{-1}$ to 20000 $h^{-1}$.

The method of the present invention includes the following processes: contacting a gaseous material containing syngas with a metal catalyst in a first reaction zone and reacting to obtain an effluent containing methanol and/or dimethyl ether; directly contacting the reaction effluent with a solid acid catalyst in the second reaction zone and reacting, or contacting the reaction effluent where was added a raw material gas containing carbon monoxide with a solid acid catalyst in the second reaction zone and reacting. After the reaction, an oxygenate product containing methyl acetate and/or acetic acid is obtained, and the product selectivity of the product methyl acetate or acetic acid is higher than 93%.

More specifically, in the method for directly producing methyl acetate and/or acetic acid from syngas, whose reaction process is carried out in at least two reaction zones and the method comprises:

a) feeding a raw material containing syngas into a first reaction zone to contact with a metal catalyst in the first reaction zone, reacting to obtain an effluent containing methanol and/or dimethyl ether;

b) allowing the effluent from the first reaction zone to enter a second reaction zone directly or after the addition of carbon monoxide so as to contact with a solid acid catalyst in the second reaction zone and react to obtain an effluent containing methyl acetate and/or acetic acid;

c) separating the effluent from the second reaction zone to obtain product of acetate and/or acetic acid, and optionally returning a residual part to enter the first reaction zone and/or the second reaction zone to recycle the reaction;

wherein the volume content of syngas feed gas in the raw material is in a range from 10% to 100%, and the volume ratio of carbon monoxide to hydrogen in the syngas is in a range from 0.1 to 10;

the reaction temperature in the first reaction zone is in a range from 180° C. to 300° C., the reaction pressure is in a range from 0.5 MPa to 20.0 MPa; and the reaction temperature in the second reaction zone is in a range from 180° C. to 300° C., the reaction pressure is in a range from 0.5 MPa to 20.0 MPa.

In the method of the present invention, the metal catalyst in the first reaction zone is a catalyst for synthesis of methanol or dimethyl ether.

In the method of the present invention, preferably, the solid acid catalyst in the second reaction zone comprises any one or any combination of zeolite molecular sieves of FER, MFI, MOR, ETL, MFS, MTF or EMT structures, or products obtained by modifying elements other than the constituent elements (such as Fe, Ga, Cu, Ag, etc.) of molecular sieve framework that meets the above characteristics or by modifying pyridine, or a mixture of multiple molecular sieves that meet the above characteristics.

Preferably, the solid acid catalyst is a hydrogen-type product of the zeolite molecular sieve, or is composed of ranging from 10% to 95% by weight of the hydrogen-type product and a remaining matrix, or is a molecular sieve product obtained by modifying the hydrogen-type product with pyridine; more preferably; the matrix is any one or a mixture of any one of alumina, silica, kaolin and magnesia.

In the method of the present invention, preferably, reactors for the first reaction zone and the second reaction zone each adopt a fixed bed reactor, preferably a tubular fixed bed reactor.

In the method of the present invention, the first reaction zone and the second reaction zone may be in the same reactor, or the first reaction zone and the second reaction zone may be in different reactors connected in series.

In the method of the present invention, in addition to carbon monoxide and hydrogen, the syngas raw material may also contain any one or more inactive gases selected from nitrogen, helium, argon and carbon dioxide. Preferably, the volume content of carbon monoxide and hydrogen is in a range from 50% to 100%; the volume percentage content of any one or more gases selected from nitrogen, helium, argon and carbon dioxide in the syngas raw material is in a range from 0% to 50%.

In a further preferred embodiment, the reaction conditions in the first reaction zone are as follows: the reaction temperature is in a range from 180° C. to 300° C., the reaction pressure is in a range from 1.0 MPa to 15.0 MPa; the reaction conditions in the second reaction zone are as follows: the reaction temperature is in a range from 180° C. to 300° C., the reaction pressure is in a range from 1.0 MPa to 15.0 MPa.

The present invention is specifically illustrated by the following examples, but the present invention is not limited to these examples.

Metal Catalyst

The metal catalyst was a copper-based catalyst, which was prepared as follows: in a beaker, 96.80 g of $Cu(NO_3)_2 \cdot 3H_2O$, 15.60 g of $Zn(NO_3)_2 \cdot 6H_2O$, and 14.71 g of $Al(NO_3)_3 \cdot 9H_2O$ were dissolved in 2000 ml of deionized water, a mixed metal nitrate aqueous solution was obtained. In another beaker, 72.62 g of strong ammonia water (25-28%) was diluted with 1500 ml of deionized water, and the ammonia solution was vigorously stirred at room temperature, and then the obtained mixed metal nitrate aqueous solution was slowly added to the ammonia solution, the addition time was about 60 min. It was filtered to obtain a precipitate, and the pH value of the precipitate was adjusted to 10.0 with another aqueous ammonia solution. After stirring for 200 minutes, it was left to age for 36 hours. Then, the precipitate was washed with deionized water to neutrality, and centrifuged. The obtained precipitate was dried in an oven at 120° C. for 24 hours. The dried sample was placed in a muffle furnace, heated to 400° C. at a temperature increase rate of 1° C./min, and roasted for 5 hours to obtain a roasted sample. 1.41 g of $Mn(NO_3)_2 \cdot 4H_2O$ and 1.36 g of $Ni(NO_3)_2 \cdot 4H_2O$ were then dissolved in 50 ml of deionized water, and the aqueous solution of manganese and nickel was loaded on the roasted sample by the dipping method, and evaporated at 80° C. to remove excess solvent. It was dried in an oven at 120° C. for 24 hours. After drying, the sample was placed in a muffle furnace, heated to 400° C. at a heating rate of 1° C./min, and calcined for 3 hours to obtain a catalyst sample, which was recorded as catalyst A.

The metal catalyst used in the present invention can also be prepared by mechanically mixing catalyst A and nano-hydrogen type ZSM-5 (Si/Al=19) at a ratio of 2:1, which was recorded as catalyst B.

Raw Material Source of Molecular Sieve

In the course of the experiment, part of the molecular sieve materials can be directly purchased commercially; part of the molecular sieve materials can be synthesized according to existing related literatures, and the specific sources are shown in Table 1.

Solid Acid Catalyst

The hydrogen-type sample was prepared as follows:

The Na-type molecular sieve in Table 1 were subjected to $NH_4NO_3$ ion exchange, dried and roasted to obtain hydrogen-type molecular sieve. For example, a preparation process for a typical hydrogen-type sample is as follows: in a hydrothermal synthesis kettle, NaMOR molecular sieve powder is added to a pre-configured 1 mol/L $NH_4NO_3$ aqueous solution with a solid-liquid mass ratio of 1:10, and was exchanged for 2 hours at 80° C. in the stirring state, filtered under vacuum and washed with water. After three consecutive exchange reactions, it was dried at 120° C. overnight and calcined for 4 hours at 550° C. to obtain the required catalyst sample HMOR.

Matrix-containing shaped hydrogen-type samples were prepared by extrusion molding. For example, the preparation process for a typical shaped sample is as follows: 80 g of Na-MOR and 20 g of alumina were thoroughly mixed, and 5-15% nitric acid was added to knead. The sample that was kneaded into a ball was extruded and shaped by an extruder. The extruded sample was dried at 120° C., and calcined at 550° C. for 4 hours, and then a hydrogen-type sample preparation method was used to prepare matrix-containing shaped hydrogen-type samples.

Pyridine-modified hydrogen-type samples were prepared. The typical preparation process was as follows: 10 g of hydrogen-type sample was charged into a reaction tube, and gradually heated to 300-550° C. under a nitrogen atmosphere of 100 mL/min, maintained for 2-6 hours, and then carried pyridine with nitrogen and treated at 200-400° C. for 2-8 hours, to obtain pyridine modified samples. The samples were labeled with H-M-py, where M represents the name of the molecular sieve.

The series of samples prepared according to the above methods are shown in Table 2.

TABLE 2

The number of the prepared sample and composition of the sample

| Catalyst No. | Catalyst | Si/Al ratio of molecular sieve | Molecular sieve content | Matrix type | Matrix content |
|---|---|---|---|---|---|
| 1# | H-MOR | 6.5 | 100% | — | 0% |
| 2# | H-MOR | 6.5 | 50% | silica + alumina + magnesia (mass ratio 2:2:1) | 50% |

TABLE 1

Sources of different molecular sieve materials and ratio of silicon-aluminum

| Molecular sieve material | Source | Way of obtaining | Si/Al ratio |
|---|---|---|---|
| NaMOR (mordenite) | The Catalyst Plant of Nankai University | purchase | 6.5 |
| NaMOR (mordenite) | The Catalyst Plant of Nankai University | purchase | 15 |
| NaSM-35 | The Catalyst Plant of Aoke | purchase | 79 |
| NaZSM-5 | The Catalyst Plant of Nankai University | purchase | 50 |
| NaEMT | Dalian Institute of Chemical Physics. | synthesis | 4 |
| NaEMT | Dalian Institute of Chemical Physics. | synthesis | 25 |
| Na-EU-12 | Dalian Institute of Chemical Physics. | synthesis | 10 |
| Na-MCM-65 | Dalian Institute of Chemical Physics. | synthesis | 50 |
| Na-MCM-35 | Dalian Institute of Chemical Physics. | synthesis | 100 |
| Na-M-MOR* | Dalian Institute of Chemical Physics. | synthesis | 16.5 |

*Na-M-MOR represents mordenite modified by elements other than the framework constituent elements prepared by in-situ synthesis, wherein M represents a modified metal atom, and the molecular sieve modified by Fe, Ga, Cu, and Ag metals are prepared during the preparation process respectively, wherein the content of the modified metal is 0.9%.

TABLE 2-continued

The number of the prepared sample and composition of the sample

| Catalyst No. | Catalyst | Si/Al ratio of molecular sieve | Molecular sieve content | Matrix type | Matrix content |
|---|---|---|---|---|---|
| 3# | H-MOR | 15 | 80% | alumina | 20% |
| 4# | H-ZSM-35 | 79 | 80% | kaolin | 20% |
| 5# | H-ZSM-5 | 50 | 70% | alumina | 30% |
| 6# | H-EMT | 4 | 80% | alumina | 20% |
| 7# | H-EMT | 25 | 80% | alumina | 20% |
| 8# | H-EU-12 | 10 | 80% | alumina | 20% |
| 9# | H-MCM-65 | 50 | 80% | alumina | 20% |
| 10# | H-MCM-35 | 100 | 90% | alumina | 10% |
| 11# | H-MOR-py | 15 | 80% | alumina | 20% |
| 12# | H-EMT-py | 25 | 80% | alumina | 20% |
| 13# | H-Fe-MOR | 16.5 | 100 | — | 0% |
| 14# | H-Cu-MOR | 16.5 | 100 | — | 0% |
| 15# | H-Ag-MOR | 16.5 | 100 | — | 0% |
| 16# | H-Ga-MOR | 16.5 | 100 | — | 0% |

Comparative Example 1

1 g of catalyst A was charged into a fixed bed reactor with an inner diameter of 16 mm, and the temperature was raised to 260° C. under a 5 vol % $H_2$+95 vol % $N_2$ atmosphere for 24 hours, and then the temperature was lowered to 220° C. The pressure of the reaction system was raised to 5 MPa with $H_2$ and CO. The flow rate under standard conditions of CO was 30 mL/min and the flow rate under standard conditions of $H_2$ was 60 mL/min. The results of the catalytic reaction were shown in Table 3.

Comparative Example 2

1 g of catalyst B was charged into a fixed bed reactor with an inner diameter of 16 mm, and the temperature was raised to 260° C. under a 5 vol % $H_2$+95 vol % $N_2$ atmosphere for 24 hours, and then the temperature was lowered to 220° C. The pressure of the reaction system was raised to 5 MPa with $H_2$ and CO. The flow rate under standard conditions of CO was 30 mL/min and the flow rate under standard conditions of $H_2$ was 60 mL/min. The results of the catalytic reaction were shown in Table 3.

Comparative Example 3

1 g of molecular sieve catalyst was charged into a fixed bed reactor with an inner diameter of 16 mm, and the temperature was raised to 240° C. under a 5 vol % $H_2$+95 vol % $N_2$ atmosphere for 24 hours, and then the temperature was lowered to 220° C. The pressure of the reaction system was raised to 5 MPa with $H_2$ and CO. The flow rate under standard conditions of CO was 30 mL/min and the flow rate under standard conditions of $H_2$ was 60 mL/min. The results of the catalytic reaction were shown in Table 3.

TABLE 3

The results of comparative examples

| Comparative example | Percent conversion of CO (%) | Selectivity for products (%) | | | | | |
|---|---|---|---|---|---|---|---|
| | | $CO_2$ | Methanol | Dimethyl ether | Methyl acetate | Acetic acid | Others |
| 1 | 27.32 | 0 | 99.87 | 0 | 0 | 0 | 0.13 |
| 2 | 38.67 | 30.94 | 0.42 | 67.38 | 0 | 0 | 1.26 |
| 3 | 0 | 0 | 0 | 0 | 0 | 0 | 0 |

Example 1

The first reaction zone and the second reaction zone were located in the same reactor, the specific reaction scheme was shown in FIG. 1, wherein the syngas as a raw material was allowed to enter the first reaction zone I to contact with the metal catalyst in the first reaction zone and react to obtain an effluent containing methanol and/or dimethyl ether; the effluent from the first reaction zone was allowed to enter the second reaction zone II to contact with the solid acid catalyst in the second reaction zone and react to obtain an effluent containing methyl acetate and/or acetic acid; the effluent from the second reaction zone was separated to obtain product of acetate and/or acetic acid; the residual part was returned to enter the first reaction zone to recycle the reaction.

1 g of copper-based catalyst A and 1 g of solid acid catalyst 11# were successively charged into the first reaction zone I (upper end) and the second reaction zone II (lower end) in a fixed bed reactor with an inner diameter of 16 mm, respectively. The temperature was raised to 260° C. under a 5 vol % $H_2$+95 vol % $N_2$ atmosphere for 24 hours, and then the temperature was adjusted to the reaction temperature (see Table 4 for details). The pressure of the reaction system was raised to 2 MPa with $H_2$ and CO. The flow rate under standard conditions of CO was 30 mL/min and the flow rate under standard conditions of $H_2$ was 60 mL/min. The results of the catalytic reaction were shown in Table 4.

TABLE 4

Reaction results at different reaction temperatures

| Reaction temperature | Percent conversion of CO (%) | Selectivity for products (%) | | | | | |
|---|---|---|---|---|---|---|---|
| | | $CO_2$ | Methanol | Dimethyl ether | Methyl acetate | Acetic acid | Others |
| 200 | 10.5 | 0.0 | 1.42 | 9.6 | 80.1 | 7.5 | 1.38 |
| 230 | 29.4 | 0.0 | 3.83 | 17.3 | 58.7 | 18.6 | 1.57 |
| 250 | 36.2 | 0.0 | 5.0 | 27.3 | 51.7 | 12.2 | 3.8 |
| 270 | 48.6 | 0.0 | 6.4 | 37.3 | 43.6 | 5.5 | 7.2 |
| 360 | 89.2 | 0.0 | 0 | 0 | 3.2 | 93.5 | 3.3 |

Example 2

Similar to the procedure of Example 1, the first reaction zone was charged with 1 g of catalyst A, and the second reaction zone was charged with 1 g of different solid acid catalysts (1-10# and 12-16#, see Table 5), and the reaction temperature was 230° C. Other conditions were the same as in Example 1. The specific reaction results were shown in Table 5.

TABLE 5

Reaction results for different molecular sieve catalysts

| Catalyst No. | Percent conversion of CO (%) | Selectivity for products (%) | | | | | |
|---|---|---|---|---|---|---|---|
| | | $CO_2$ | Methanol | Dimethyl ether | Methyl acetate | Acetic acid | Others |
| 1# | 26.8 | 0.0 | 0.23 | 9.78 | 72.40 | 17.14 | 0.45 |
| 2# | 17.6 | 0.0 | 0.12 | 14.9 | 71.50 | 12.95 | 0.53 |
| 3# | 13.5 | 0.0 | 0.05 | 8.70 | 85.78 | 5.26 | 0.21 |
| 4# | 21.4 | 0.0 | 0.90 | 15.60 | 62.30 | 19.30 | 1.90 |
| 5# | 15.8 | 0.0 | 2.80 | 68.70 | 3.20 | 0.00 | 28.5 |
| 6# | 23.3 | 0.0 | 1.10 | 11.80 | 62.30 | 23.5 | 1.30 |
| 7# | 25.8 | 0.0 | 0.90 | 8.65 | 63.80 | 24.53 | 2.12 |
| 8# | 20.1 | 0.0 | 0.10 | 23.50 | 75.10 | 1.10 | 0.20 |
| 9# | 17.6 | 0.0 | 0.38 | 31.60 | 63.10 | 4.53 | 0.39 |
| 10# | 18.7 | 0.0 | 0.69 | 27.90 | 68.20 | 2.32 | 0.89 |
| 12# | 31.2 | 0.0 | 0.81 | 10.30 | 68.70 | 19.8 | 0.39 |
| 13# | 16.1 | 1.8 | 2.90 | 16.31 | 60.7 | 17.73 | 2.37 |
| 14# | 17.3 | 5.6 | 0.63 | 14.42 | 59.6 | 19.18 | 0.57 |
| 15# | 16.8 | 0.7 | 1.83 | 11.80 | 61.3 | 24.16 | 0.21 |
| 16# | 15.9 | 0.3 | 0.56 | 13.38 | 60.2 | 25.05 | 0.51 |

Example 3

Similar to the procedure of Example 1, 1 g of copper-based catalyst A and 1 g of molecular sieve catalyst 11# were successively charged into the upper end and the lower end in the fixed bed reactor with an inner diameter of 16 mm. The temperature was raised to 260° C. under a 5 vol % $H_2$+95 vol % $N_2$ atmosphere for 24 hours, and then the temperature was lowered to 230° C. The pressure of the reaction system was raised with $H_2$ and CO (see Table 6). The flow rate under standard conditions of CO was 30 mL/min and the flow rate under standard conditions of $H_2$ was 30 mL/min. The results of the catalytic reaction were shown in Table 6.

TABLE 6

Reaction results at different reaction pressures

| Reaction pressure | Percent conversion of CO (%) | Selectivity for products (%) | | | | | |
|---|---|---|---|---|---|---|---|
| | | $CO_2$ | Methanol | Dimethyl ether | Methyl acetate | Acetic acid | Others |
| 1 | 21.3 | 0.0 | 6.93 | 22.1 | 53.7 | 15.6 | 1.67 |
| 5 | 33.4 | 0.0 | 2.7 | 12.9 | 63.7 | 19.6 | 1.10 |
| 8 | 36.8 | 0.0 | 0.1 | 8.8 | 71.7 | 19.1 | 0.3 |
| 15 | 53.8 | 0.0 | 0.1 | 1.8 | 95.7 | 2.2 | 0.2 |

Example 4

Similar to the procedure of Example 1, 1 g of copper-based catalyst A and 1 g of molecular sieve catalyst 11# were successively charged into the upper end and the lower end in the fixed bed reactor with an inner diameter of 16 mm. The temperature was raised to 260° C. under a 5 vol % $H_2$+95 vol % $N_2$ atmosphere for 24 hours, and then the temperature was lowered to 230° C. The pressure of the reaction system was raised to 2 MPa with $H_2$ and CO. The total flow rate under standard conditions of CO and $H_2$ was 60 mL/min. The ratios of CO to $H_2$ were shown in Table 7. The results of the catalytic reaction were shown in Table 7.

TABLE 7

Reaction results under different ratios of $CO/H_2$

| CO/ $H_2$ | Percent conversion of CO (%) | $CO_2$ | Selectivity for products (%) | | | | |
|---|---|---|---|---|---|---|---|
| | | | Meth-anol | Dimethyl ether | Methyl acetate | Acetic acid | Others |
| 0.5 | 32.3 | 0.0 | 6.6 | 45.5 | 38.3 | 7.5 | 2.1 |
| 2 | 18.7 | 0.0 | 2.71 | 10.7 | 62.2 | 21.8 | 2.59 |
| 3 | 9.6 | 0.0 | 0.98 | 3.5 | 78.3 | 16.6 | 0.62 |
| 8 | 3.6 | 0.0 | 0 | 1.5 | 94.8 | 3.5 | 0.2 |
| 10 | 2.5 | 0.0 | 0 | 1.4 | 94.9 | 3.6 | 0.1 |

Example 5

Similar to the procedure of Example 1, 1 g of catalyst and 1 g of molecular sieve catalyst 11# were successively charged into the upper end and the lower end in the fixed bed reactor with an inner diameter of 16 mm. The temperature was raised to 260° C. under a 5 vol % $H_2$+95 vol % $N_2$ atmosphere for 24 hours, and then the temperature was lowered to 230° C. The pressure of the reaction system was raised to 2 MPa. The ratio of CO to $H_2$ was 3, and the reaction atmosphere also contained methanol and dimethyl ether. The total gas flow rate was 60 ml/min under standard conditions. The specific ratios were shown in the table. The selectivity of methanol and dimethyl ether was not calculated in the reaction product. The results of the catalytic reaction were shown in Table 8.

TABLE 8

Reaction results when the reaction atmosphere contained methanol and dimethyl ether

| CO (ml/min) | Meth-anol (ml/min) | Di-methyl ether (ml/min) | Percent conversion of CO (%) | $CO_2$ | Selectivity for products (%) | | |
|---|---|---|---|---|---|---|---|
| | | | | | Methyl acetate | Acetic acid | Others |
| 40 | 0 | 6.7 | 13.4 | 0 | 97.1 | 2.4 | 0.5 |
| 40 | 6.7 | 0 | 10.2 | 0 | 77.9 | 21.6 | 0.5 |

Example 6

Similar to the procedure of Example 1, 1 g of catalyst and 1 g of molecular sieve catalyst 11# were successively charged into the upper end and the lower end in the fixed bed reactor with an inner diameter of 16 mm. The temperature was raised to 260° C. under a 5 vol % $H_2$+95 vol % $N_2$ atmosphere for 24 hours, and then the temperature was lowered to setting 250° C. The pressure of the reaction system was raised by 2 MPa with $H_2$ and CO. The ratio of CO to $H_2$ was 3. The total gas flow rate and the results of the catalytic reaction were shown in Table 9.

TABLE 9

Reaction results at different reaction space velocities

| Total gas flow rate (ml/min) | Percent conversion of CO (%) | $CO_2$ | Selectivity for products (%) | | | | |
|---|---|---|---|---|---|---|---|
| | | | Meth-anol | Di-methyl ether | Methyl acetate | Acetic acid | Others |
| 0 | 22.1 | 0.0 | 2.01 | 5.5 | 63.3 | 25.8 | 3.39 |
| 120 | 9.6 | 0.0 | 6.01 | 27.5 | 48.3 | 17.5 | 0.69 |
| 650 | 3.8 | 0.0 | 9.2 | 30.5 | 45.3 | 14.3 | 0.7 |

Example 7

Similar to the procedure of Example 1, different amounts (see Table 10 in detail) of copper-based catalyst A and different amounts (see Table 10 in detail) of catalyst 11# were successively charged into the upper end and the lower end in the fixed bed reactor with an inner diameter of 16 mm. The temperature was raised to 260° C. under a 5 vol % $H_2$+95 vol % $N_2$ atmosphere for 24 hours, and then the temperature was lowered to setting 230° C. The pressure of the reaction system was raised to 2 MPa with $H_2$ and CO. The flow rate under standard conditions of CO was 30 mL/min and the flow rate under standard conditions of $H_2$ was 30 mL/min. The results of the catalytic reaction were shown in Table 10.

TABLE 10

Reaction results with different catalyst loading ratios

| Catalyst | | Percent con-version of CO (%) | $CO_2$ | Selectivity for products (%) | | | | |
|---|---|---|---|---|---|---|---|---|
| A | 11# | | | Meth-anol | Di-methyl ether | Methyl acetate | Acetic acid | Others |
| 1 | 2 | 34.6 | 0.0 | 0.8 | 5.3 | 85.9 | 7.1 | 0.9 |
| 1 | 3 | 38.9 | 0.0 | 0.5 | 2.1 | 89.1 | 7.6 | 0.7 |
| 1 | 5 | 42.5 | 0.0 | 0.1 | 1.5 | 91.0 | 7.2 | 0.2 |
| 2 | 1 | 41.7 | 0.0 | 10.3 | 39.7 | 45.2 | 4.3 | 0.5 |
| 3 | 1 | 55.8 | 0.0 | 15.7 | 42.3 | 41.0 | 0.9 | 0.1 |

Example 8

Figure 2:
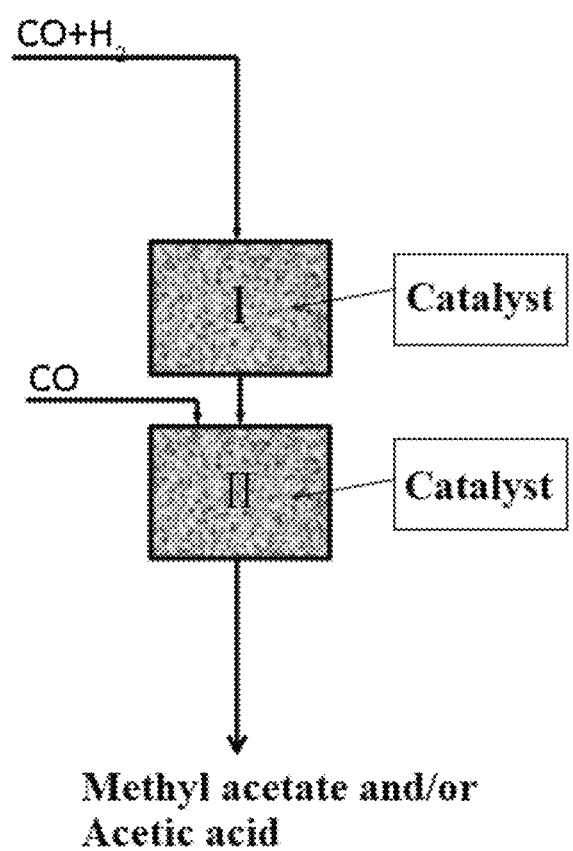
FIG. 2 is a flow chart of the direct preparation of methyl acetate/acetic acid from syngas according to another embodiment of the present invention, wherein the first reaction zone and the second reaction zone are in different reactors.

The procedure was similar to that of Example 1, except that the first reaction zone I and the first reaction zone II were located in different fixed bed reactors. Specifically, referring to FIG. 2, the reaction process was basically similar to the process described in Example 1 with respect to FIG. 1. 1 g of copper-based catalyst A and 1 g of carbonylation molecular sieve catalyst 11# were successively charged into the first reactor and the second reactor, respectively, wherein the inner diameter of the reactors was 16 mm. The catalyst in the first reaction zone was heated to 260° C. under a 5 vol % $H_2$+95 vol % $N_2$ atmosphere for 24 hours, and then the temperature was lowered. The pressure of the reaction system was raised to 2 MPa with $H_2$ and CO. The feed conditions in the first reaction zone were as follows. The reaction temperature was 250° C. The flow rate under standard conditions of CO was 30 mL/min and the flow rate under standard conditions of $H_2$ was 60 mL/min. The effluent from the first reaction zone entered the second reaction zone, while carbon monoxide was added to the second reaction zone (standard conditions 30 mL/min), the effluent from the first reaction zone and the added carbon monoxide entered the second reaction zone together. The reaction results at the temperatures of 190, 210, 230, 280, and 300° C. in the second reactor were shown in Table 11.

TABLE 11

Reaction results at different reaction temperatures in the second reaction zone

| Reaction temperature (° C.) | Percent conversion of CO (%) | $CO_2$ | Methanol | Dimethyl ether | Methyl acetate | Acetic acid | Others |
|---|---|---|---|---|---|---|---|
| 190 | 27.50 | 0.0 | 1.20 | 78.3 | 20.2 | 0.00 | 0.3 |
| 210 | 33.75 | 0.0 | 0.05 | 28.6 | 71.8 | 0.00 | 0.45 |
| 230 | 40.00 | 0.0 | 0.00 | 0.0 | 66.7 | 32.4 | 0.9 |
| 280 | 48.75 | 0.0 | 0.00 | 0.0 | 5.3 | 93.7 | 1.0 |
| 300 | 50.00 | 0.0 | 0.00 | 0.0 | 0.00 | 98.5 | 1.5 |

Example 9

The procedure was similar to that of Example 1, except that the first reaction zone I and the first reaction zone II were located in different fixed bed reactors. Specifically, referring to FIG. 2, the reaction process was similar to the process described in Example 1 with respect to FIG. 1.

1 g of copper-based catalyst A and 1 g of carbonylation molecular sieve catalyst 11# were successively charged into the first reactor and the second reactor, respectively, wherein the inner diameter of the reactors was 16 mm. The catalyst in the first reaction zone was heated to 260° C. under a 5 vol % $H_2$+95 vol % $N_2$ atmosphere for 24 hours. When the temperature was then lowered to 190, 220, 250, 280 and 300° C., the pressure of the reaction system was raised to 2 MPa with $H_2$ and CO. The feed conditions in the first reaction zone were as follows. The flow rate under standard conditions of CO was 30 mL/min and the flow rate under standard conditions of $H_2$ was 60 mL/min. The effluent from the first reaction zone entered the second reaction zone, while carbon monoxide was added to the second reaction zone (standard conditions 30 mL/min); the effluent from the first reaction zone and the added carbon monoxide entered the second reaction zone together. The reaction results at the temperature of 230° C. in the second reactor were shown in Table 12.

TABLE 12

Reaction results at different reaction temperatures in the first reaction zone

| Reaction temperature (° C.) | Percent conversion of CO (%) | $CO_2$ | Methanol | Dimethyl ether | Methyl acetate | Acetic acid | Others |
|---|---|---|---|---|---|---|---|
| 190 | 12.00 | 0.0 | 0.0 | 0.00 | 0.00 | 99.5 | 0.5 |
| 220 | 31.00 | 0.0 | 0.05 | 0.00 | 0.00 | 99.3 | 0.45 |
| 250 | 43.33 | 0.0 | 0.00 | 0.00 | 73.6 | 25.5 | 0.9 |
| 280 | 53.60 | 0.0 | 0.00 | 15.27 | 82.85 | 0.88 | 1.0 |
| 300 | 63.50 | 0.0 | 0.00 | 32.37 | 65.43 | 0.70 | 1.5 |

Example 10

The procedure was similar to that of Example 1, except that the first reaction zone I and the first reaction zone II were located in different fixed bed reactors. Specifically, referring to FIG. 2, the reaction process was similar to the process described in Example 1 with respect to FIG. 1.

Copper-based catalyst A and carbonylation molecular sieve catalyst 11# were successively charged into the first reactor and the second reactor, respectively, see Table 10 for the catalyst loading. The inner diameter of the reactors was 16 mm. The catalyst in the first reaction zone was heated to 260° C. under a 5 vol % $H_2$+95 vol % $N_2$ atmosphere for 24 hours. When the temperature was then lowered to 230° C., the pressure of the reaction system was raised to 5 MPa with $H_2$ and CO. The feed conditions in the first reaction zone were as follows. The flow rate under standard conditions of CO was 30 mL/min and the flow rate under standard conditions of $H_2$ was 60 mL/min. The effluent from the first reaction zone entered the second reaction zone, while carbon monoxide was added to the second reaction zone (standard conditions 30 mL/min); the effluent from the first reaction zone and the added carbon monoxide entered the second reaction zone together. The reaction results at the temperature of 230° C. in the second reactor were shown in Table 13.

TABLE 13

Reaction results at different reaction temperatures in the first reaction zone

| Catalyst A | Catalyst 11# | Percent conversion of CO (%) | $CO_2$ | Methanol | Dimethyl ether | Methyl acetate | Acetic acid | Others |
|---|---|---|---|---|---|---|---|---|
| 1 | 2 | 60.2 | 0.00 | 0.00 | 0.00 | 48.20 | 51.70 | 0.1 |
| 1 | 3 | 66.7 | 0.00 | 0.00 | 0.00 | 16.12 | 83.73 | 0.15 |
| 1 | 5 | 70.8 | 0.00 | 0.00 | 0.00 | 2.38 | 97.12 | 0.5 |
| 2 | 1 | 57.2 | 0.00 | 0.00 | 30.18 | 69.02 | 0.00 | 0.8 |
| 3 | 1 | 63.3 | 0.00 | 0.00 | 40.04 | 59.06 | 0.00 | 0.9 |

Example 11

The procedure was similar to that of Example 1, except that the first reaction zone I and the first reaction zone II were located in different fixed bed reactors. Specifically, referring to FIG. 2, the reaction process was similar to the process described in Example 1 with respect to FIG. 1.

1 g of copper-based catalyst B and 1 g of carbonylation molecular sieve catalyst 11# were successively charged into the first reactor and the second reactor, respectively, wherein the inner diameter of the reactors was 16 mm. The catalyst in the first reaction zone was heated to 260° C. under a 5 vol % $H_2$+95 vol % $N_2$ atmosphere for 24 hours. When the temperature was then lowered to 230° C., the pressure of the reaction system was raised to 5 MPa with $H_2$ and CO. The feed conditions in the first reaction zone were as follows. The flow rate under standard conditions of CO was 30 mL/min and the flow rate under standard conditions of $H_2$ was 60 mL/min. The effluent from the first reaction zone entered the second reaction zone, while carbon monoxide was added to the second reaction zone (standard conditions 30 mL/min); the effluent from the first reaction zone and the added carbon monoxide entered the second reaction zone together. The reaction results at the temperature of 230° C. in the second reactor were shown in Table 14.

TABLE 14

Reaction results when catalyst B was loaded in the first reaction zone

| Percent conversion of CO (%) | Selectivity for products (%) | | | | |
|---|---|---|---|---|---|
| | $CO_2$ | Methanol | Dimethyl ether | Methyl acetate | Acetic acid | Others |
| 40.2 | 29.2 | 0.00 | 0.00 | 69.3 | 0.8 | 0.7 |

The present invention has been described in detail above, but the present invention is not limited to the specific embodiments described herein. Those skilled in the art can understand that other changes and modifications can be made without departing from the scope of the invention. The scope of the invention is defined by the appended claims.

What is claimed is:

1. A method for directly producing acetic acid from syngas, whose reaction process is carried out in at least two reaction zones, the method comprising:
   a) feeding a raw material containing syngas into a first reaction zone comprising a copper-based metal catalyst and contacting and reacting the syngas with the copper-based metal catalyst in the first reaction zone to obtain an effluent containing methanol;
   b) feeding the effluent from the first reaction zone to a second reaction zone comprising a solid acid catalyst, either directly or after the addition of carbon monoxide to said effluent, and contacting and reacting the effluent from the first reaction zone with the solid acid catalyst in the second reaction zone to obtain an effluent containing acetic acid;
   c) separating the acetic acid product from the effluent obtained from the second reaction zone, and optionally returning a residual part of the effluent from the second reaction zone to the first reaction zone and/or second reaction zone as one or more recycle streams;
   wherein the volume content of syngas in the raw material is in a range from 10% to 100%, and the volume ratio of carbon monoxide to hydrogen in the syngas is in a range from 0.1 to 10;
   the reaction temperature in the first reaction zone is in a range from 190° C. to 230° C., and the reaction pressure is in a range from 1.0 MPa to 8.0 MPa; and the reaction temperature in the second reaction zone is in a range from 230° C. to 300° C., and the reaction pressure is in a range from 1.0 MPa to 8.0 MPa;
   wherein the solid acid catalyst in the second reaction zone comprises one or more zeolite molecular sieves selected from MTF and EMT zeolite molecular sieves, and wherein the zeolite molecular sieve may also be modified with pyridine or elements other than the framework constituent elements.

2. The method of claim 1, wherein the solid acid catalyst is a hydrogen-type product of the one or more zeolite molecular sieves, optionally further comprising a matrix, or a zeolite molecular sieve product obtained by modifying a hydrogen-type product of the one or more zeolite molecular sieves with pyridine, wherein the matrix is selected from alumina, silica, kaolin, magnesia and combinations thereof and when the matrix is present the catalyst comprises 10% to 95% by weight of the hydrogen-type product with the remainder being the matrix.

3. The method of claim 1, wherein the first reaction zone and/or the second reaction zone are in a fixed bed reactor.

4. The method of claim 1, wherein the first reaction zone and the second reaction zone are in a same fixed bed reactor, or the first reaction zone and the second reaction zone are respectively in different reactors connected in series.

5. The method of claim 1, wherein the raw material comprises from 50% to 100% by volume of carbon monoxide and hydrogen and from 0% to 50% by volume of one or more inactive gases selected from nitrogen, helium, argon and carbon dioxide.

6. The method of claim 3, wherein the fixed bed reactor is a tubular fixed bed reactor.

* * * * *